US005872527A

United States Patent [19]
Yanagisawa

[11] Patent Number: 5,872,527
[45] Date of Patent: Feb. 16, 1999

[54] MEDICAL KEYBOARD APPARATUS PROVIDED WITH DATA INPUTTING MECHANICAL SWITCHES AND FUNCTION EXECUTING FLAT SWITCHES

[75] Inventor: Satoshi Yanagisawa, Hachioji, Japan

[73] Assignee: Olympus Optical Co., Ltd., Tokyo, Japan

[21] Appl. No.: 826,385

[22] Filed: Apr. 9, 1997

Related U.S. Application Data

[63] Continuation of Ser. No. 519,702, Aug. 28, 1995, abandoned.

[30] Foreign Application Priority Data

Oct. 20, 1994 [JP] Japan .................................. 6-255771

[51] Int. Cl.⁶ .................................................. H03K 17/94
[52] U.S. Cl. ....................................... 341/22; 341/34
[58] Field of Search ............................ 341/22, 23, 27, 341/31, 32, 33, 34; 345/168, 173; 400/713, 714, 477, 496

[56] References Cited

U.S. PATENT DOCUMENTS

| | | | |
|---|---|---|---|
| 3,890,480 | 6/1975 | Berling et al. | 400/713 |
| 4,101,883 | 7/1978 | Hempeius et al. | 341/22 |
| 4,274,081 | 6/1981 | Nomura et al. | 341/22 |
| 4,523,060 | 6/1985 | Maguire | 341/22 |
| 4,698,618 | 10/1987 | Liuzzo et al. | 341/22 |
| 5,231,380 | 7/1993 | Logan . | |
| 5,378,069 | 1/1995 | Bowen | 400/477 |

FOREIGN PATENT DOCUMENTS 1-175832   7/1989   Japan .

*Primary Examiner*—Michael Horabik
*Assistant Examiner*—Andrew Hill
*Attorney, Agent, or Firm*—Armstrong, Westerman, Hattori, McLeland & Naughton

[57] ABSTRACT

Keys forming a data inputting part to input such data as characters are formed of mechanical switches large in the operating stroke so that data of many inputting key operations may be input by a blind touch and keys forming a function executing part to execute preset functions are formed of flat switches having substantially no operating stroke and covered with a water-proof cover so as to be able to be simply cleaned even in case the functions are operated to be executed with dirty hands while the medical apparatus is being used.

14 Claims, 8 Drawing Sheets

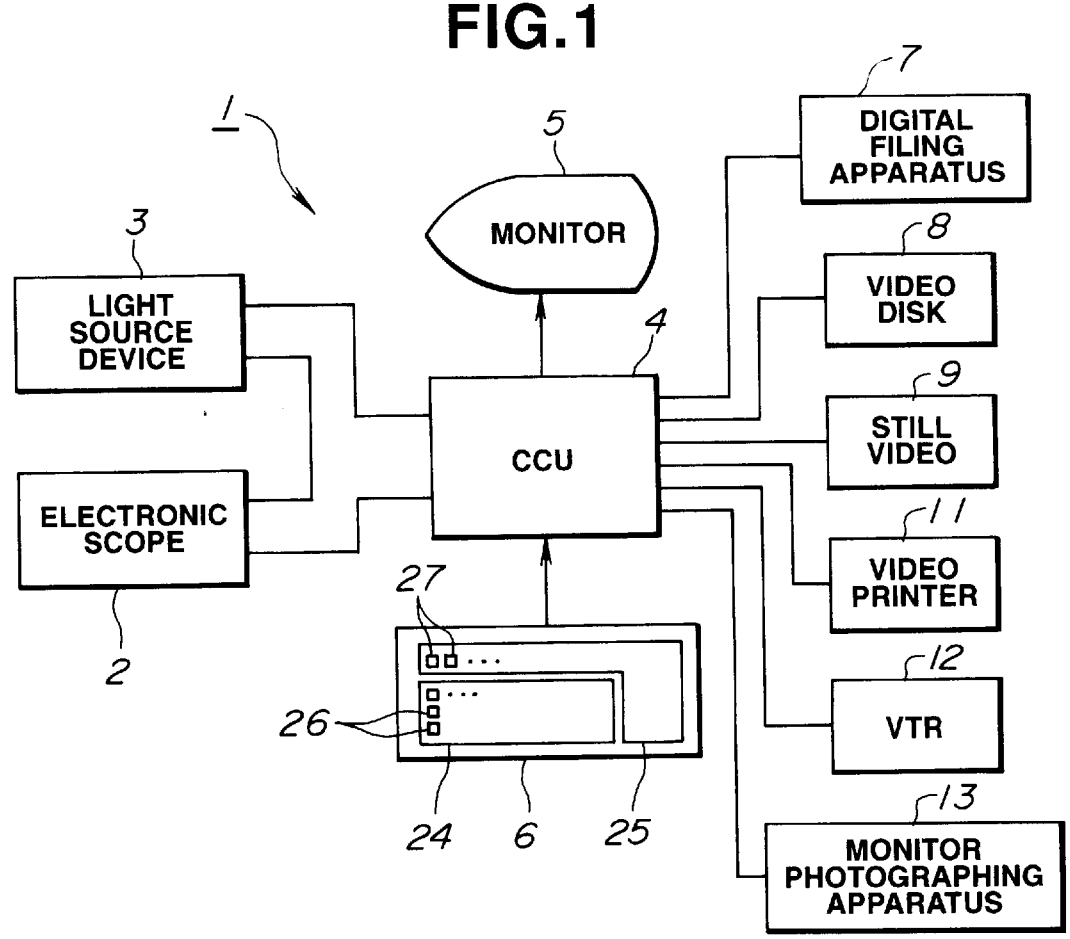
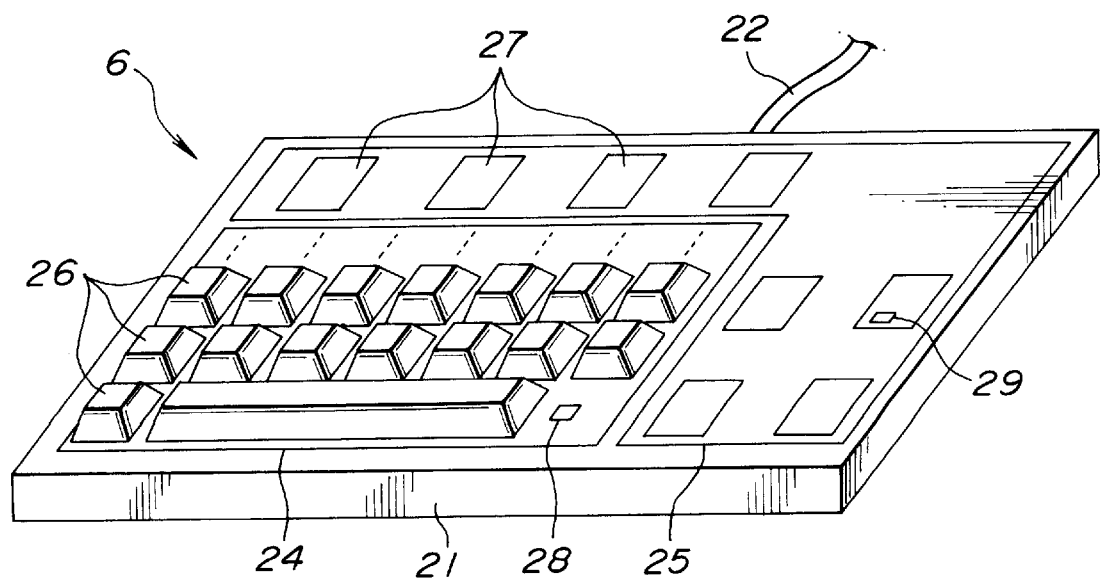

MEDICAL KEYBOARD APPARATUS PROVIDED WITH DATA INPUTTING MECHANICAL SWITCHES AND FUNCTION EXECUTING FLAT SWITCHES

This application is a continuation of application Ser No. 08/519,702 filed Aug. 28, 1995, now abandoned.

BACKGROUND OF THE INVENTION

Field of the Invention and Description of Related Arts

This invention relates to a medical keyboard apparatus used for such medical system as an electronic endoscope system and provided with data inputting mechanical switches and function executing flat switches.

Recently, in such medical electric apparatus or medical electric system as an electronic endoscope system, it is general to form a system having a function of recording in a recording medium diagnosis data to prepare or effectively utilize clinical charts so as to be made a data base and to be able to be referred to in the later diagnosis or the like. In such case, a keyboard is extensively used to prepare patient data.

The keyboard used in the medical field, that is, the medical keyboard is used to input a comment on each inspected (or diagnosed) patient. In the case of the medical keyboard, during the medically inspecting operation, the medical keyboard will be likely to be polluted, particularly the inspected patient may be suffering from an infectious disease and therefore it is necessary to set the keyboard in a clean state.

Conventionally used is a mechanical type keyboard (in the journal of Japanese Patent Application Laid Open No. 175832/1989) formed of only mechanical switches high in the operability or flat type keyboard formed of only flat switches easy to maintain in a sanitary state.

The mechanical type keyboard formed of only mechanical switches has a merit of a high operability that it can be operated with a blind touch. However, it is not of a waterproof structure and is therefore of a structure likely to be covered with dusts or polluted. It requires a trouble to remove dusts. In case it is polluted, the sterilization with a sterilizing liquid will be a trouble.

On the other hand, the flat type keyboard is easy to be made of a water-proof structure. When it is made of a water-proof structure, even if it has dusts deposited or is operated by hand likely to be polluted during the inspection, when the keyboard is wiped with a sterilizing liquid, it will be able to simply have the dusts removed and to be sterilized.

However, in the flat type keyboard, in case the flat switches are operated, the movement of such movable members as the mechanical switches will be hardly able to be sensed by the touch of the operating finger and therefore its operability will be lower than of the mechanical type keyboard. Therefore, the flat type keyboard can not be substantially operated with a blind touch as in the case of the mechanical type keyboard. Therefore, in the case of the operation it will be necessary to perceive whether the operation is carried out or not.

In most cases, the medical keyboard is provided with data inputting keys mostly inputting characters and signs and function execution inputting keys executing functions. These data inputting keys and function execution inputting keys are different in the using frequency in response to the environment in which the medical keyboard is used.

In the medical keyboard used in such medical apparatus as, for example, an endoscope system, when a view or comment after the examination is to be input, data will be mostly input or, during the examination or diagnosis, a function for executing the examination or diagnosis will be mostly executed.

In such case, during the examination, the hands will be in a dirty state and therefore the keys which will be able to be simply cleaned even if operated with dirty hands will be desirable. If the function executing keys can execute one independent function with one key operation, they need not be able to be operated with a blind touch.

On the other hand, as such data as views or comments are input mostly after the examination, it is preferable that the data can be simply input (with non-dirty hands) to that inputting the data with dirty hands can be simply cleaned.

On the other hand, in the prior reference, for the data inputting keys and function execution inputting keys, under any environment, there can be selected and used the formation of only the mechanical switch or the formation of only the flat switch and therefore there is a defect that, in case the using frequencies of the data inputting keys and function execution inputting keys are different, the keys will not be able to be used as set in a more pertinent operating state.

Also, in the prior reference, it is very significant that the user has a little freedom to select a medical keyboard apparatus adapted to the environment and is provided with a medical keyboard apparatus of a higher multiplicity.

On the other hand, a mechanical type keyboard to which a touch panel is attached as an option as combined is disclosed in U.S. Pat. No. 5,231,380. This touch panel is to put data into a computer and is provided with keys arranged on the periphery of an ordinary keyboard and hard to operate so as to be used as fitted to a position easy to operate.

Therefore, in the patent of this prior reference, data can be input in a position easy to operate but by the touch panel and therefore the data can not be input by a blind touch. That is to say, the data input is different from the operation of executing the function set in advance and, in general, many data are continuously input. Therefore, the mechanical type keyboard wherein data can be input by a blind touch is preferable. This prior reference apparently resembles the keyboard of the present application but its function is different and the following objects can not be well attained in the reference.

OBJECTS AND SUMMARY OF THE INVENTION

An object of the present invention is to provide a medical keyboard apparatus wherein keys of many input key operating times such as in inputting data can be operated for input and keys anticipated to be operated in a dirty environment and capable of executing the function with one time key inputting operation can be simply set in a clean state.

Another object of the present invention is to provide the user with a medical keyboard apparatus wherein data inputting keys and function execution inputting keys can be selected and used in response to the using environment.

The medical keyboard apparatus of the present invention is used for a medical electric apparatus and comprises:
  a data inputting part for inputting data including characters and signs;
  a function execution inputting part for inputting instructions to execute a preset function for the medical electric apparatus;

a plurality of mechanical switches forming said data inputting part and having a long stroke on which a contact is switched; and a plurality of flat switches forming said function execution inputting part, having substantially no stroke on which a contact is switched and having a water-proof function.

Therefore, the data of many key input operating times can be input with a blind touch by operating the mechanical switch and the key inputting operation to execute the function anticipated to be used under such dirty environment as in using the medical apparatus can be simply set in a clean state by the flat switch covered with a water-proof cover.

BRIEF DESCRIPTION OF THE DRAWINGS

FIGS. 1 to 5B relate to the first embodiment of the present invention. FIG. 1 is a block diagram showing the formation of an electronic endoscope system provided with the first embodiment.

FIG. 2 is a block diagram showing the more particular formation of the electronic endoscope.

FIG. 3 is a plan view showing a medical keyboard apparatus of the first embodiment.

FIG. 4 is a perspective view showing the schematic formation of the medical keyboard apparatus.

FIG. 5B is a sectioned view showing the structure of a flat switch.

FIG. 7 is a perspective view showing the schematic formation of a medical keyboard apparatus of the second embodiment.

FIG. 8 is an elevation showing the schematic formation of the medical keyboard apparatus.

FIG. 11 is a perspective view showing the schematic formation of a medical keyboard apparatus of the fourth embodiment.

FIG. 12 is an elevation showing the schematic formation of the medical keyboard apparatus.

DETAILED DESCRIPTION OF THE PREFERRED EMBODIMENTS

The embodiments of the present invention shall be concretely described in the following with reference to the drawings.

Figure 2:
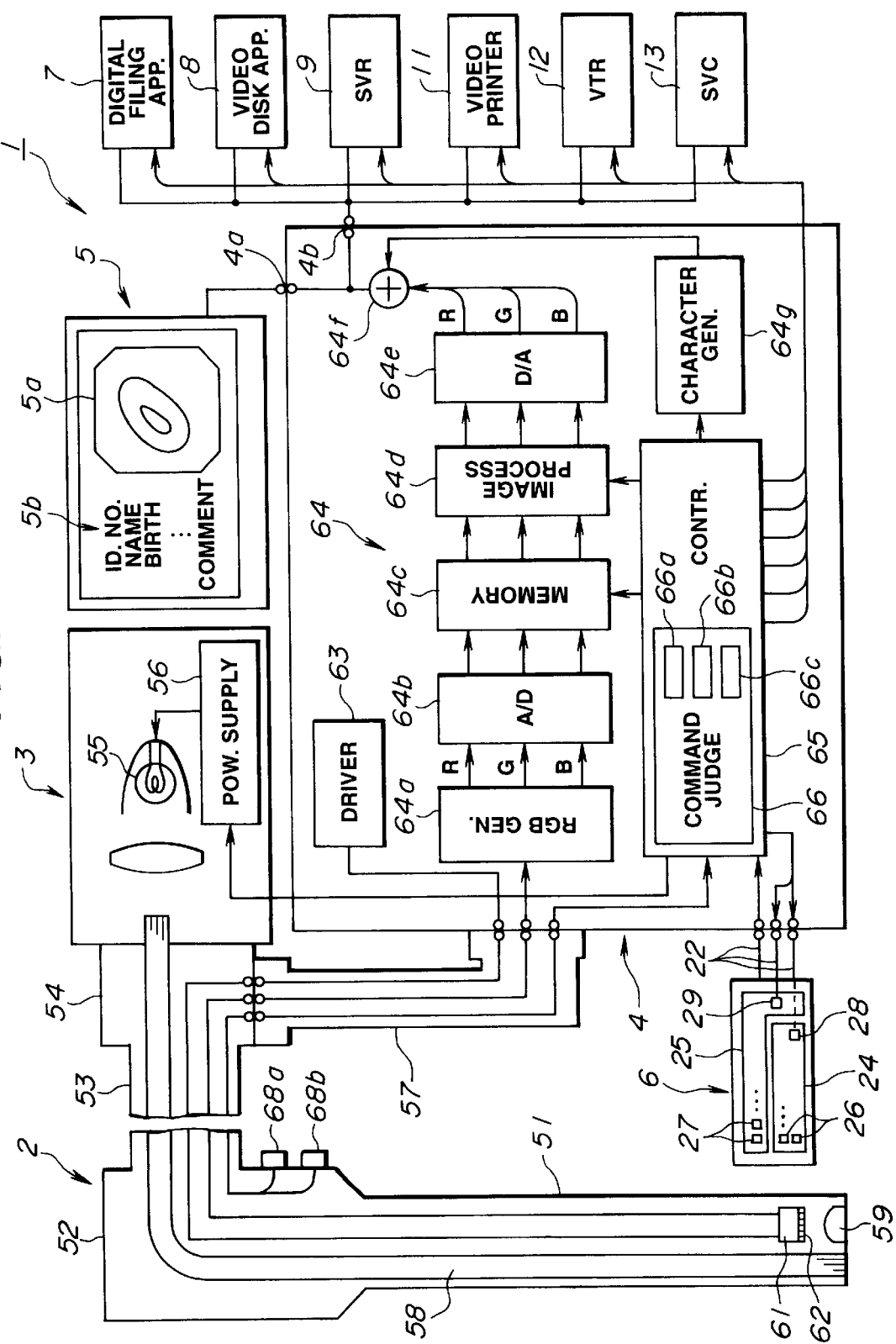

As shown in FIGS. 1 and 2, an electronic endoscope system 1 provided with the first embodiment of the present invention has an electronic endoscope (abbreviated as an electronic scope or merely as a scope) 2, a light source device 3 feeding an illuminating light to this scope 2, a camera controlling unit (abbreviated as a CCU hereinafter) 4, a color monitor 5 wherein a video signal produced by this CCU 4 is input and an endoscope image is displayed on a displaying surface and a medical keyboard apparatus (abbreviated merely as a keyboard hereinafter) 6 of the first embodiment removably connected with the CCU 4 and inputting data and has peripheral apparatus or peripheral devices connected with the CCU 4.

That is to say, the electronic endoscope system 1 has a digital filing apparatus 7 connected with the CCU 4 and filing digital picture images, a video disc apparatus 8 recording/reproducing picture images in a video disk, a still video recorder 9 recording/reproducing still pictures, a video printer 11 printing endoscope images, a VTR 12 recording/reproducing video signals and a monitor photographing apparatus 13 photographing the same endoscope picture images as are displayed in the color monitor 5.

As shown in FIG. 2, the scope 2 comprises an inserted part 51 inserted into the body cavity of a patient to be examined with the endoscope, an operating part 52 of a thick width to be gripped by the operator to make an inserting operation and bending operation and a universal cord 53 extended out of this operating part 52 so that, when a connector 54 provided at the distal end of the universal cord 53 is connected to the light source device 3, a white illuminating light from a lamp within the light source device will be fed as concentrated through a lens. This lamp 55 is fed with a light emitting electric power from the electric source 56.

A signal cable 57 is extended out of this connector 54 to a signal connector provided at the distal end of the signal cable 57 is connected to the CCU 4.

The illuminating light fed from the lamp 55 of the light source device 3 is transmitted by a light guide 58 inserted through the scope 2 and is projected on the side of the examined part position of the affected part in front from the distal end fitted to an illuminating window provided at the distal end of the inserted part 51. The examined part position illuminated by the illuminating light having passed through the illuminating window forms an optical image on the focal plane of an objective lens 59 fitted to an observing window adjacent to the illuminating window. A charge coupled device (abbreviated as a CCD) 61 as a solid state imaging device is arranged on this focal plane and the optical image is photoelectrically converted. A mosaic filter 62 is arranged in front of the photoelectrically converting surface of this CCD 61 and optically separates colors of each pixel.

The photoelectrically converted signal is read out by impressing a driving signal from a driver 63 within the CCU 4, a video signal is produced by a video signal processing circuit 64 within the CCD 4, this video signal is put into the color monitor 5 through the cable connected to the video signal outputting end 4a and the endoscope picture image taken on the displaying surface is displayed.

The above mentioned video signal processing circuit 64 has an RGB producing circuit 64a producing, for example, R, G, B signals from the output signal of the CCD 61, an A/D converter 64b respectively A/D converting the R, G, B signals, a memory 64c respectively temporarily memorizing the digital R, G, B signals, a picture image processing circuit 64d processing such as zooming the picture image data memorized in the memory 64c under the control by a controller 65 and a D/A converter 64e converting the digital R, G, B signals having passed through this picture image processing circuit 64d to analogue R, G, B signals which are output to the color monitor 5 through an adder 64f.

When this adder 64f is connected with the outputting end of a character generating circuit 64g and such character as a letter or sign is output, the character will be added to the R, G, B signals and will be output to the color monitor 5 or the like.

The keyboard 6 of the first embodiment inputting such data as characters consisting of letters and signs and instructing to execute a predetermined function is connected with the controller 65 within the CCU 4. This controller 65 has a command judging part which judges whether the input data input from the keyboard 6 are commands corresponding to the preset function or such data as an ID number, name and comment displayed together with the endoscope picture image or not. The command judging part 66 has a function 66a of judging the command of switching the displaying form in the color monitor 5, a function 66b of judging the command of a plurality of functions by the scope 2 and CCU 4 and a function 66c of judging the command of controlling the functions of the peripheral devices connected to the CCD 4.

As described later, the displaying form switching command judging function 66a is a function of judging, for example, a command of switching a display in colors and a monochromatic display, a color bar displaying/erasing command and a cursor displaying/erasing command. Also, the function 66b of judging the command of a plurality of functions by the scope 2 and CCU 4 is a function of judging a moving picture/still picture switching command and a command of displaying a picture image in the central position of a monitor picture. Also, the peripheral device controlling command judging function 66c is a function of judging whether the command is a command controlling recording and reproducing pictures by the peripheral device.

In case the command is judged to be such, the controller 65 will make the corresponding control. In case the flat switch 27 of the function execution inputting part 25 instructing to execute the predetermined function is operated, when the controller 65 judges this input, an LED 28 provided on the keyboard 6 will light and will make the corresponding control.

When this LED 28 lights, the user such as the operator will be able to confirm whether the operation of the flat switch 27 has been accepted or not. That is to say, the flat switch 27 has substantially no operating stroke from OFF to ON (that is to say, the user can not substantially distinguish the operating stroke from the operating finger touch) and therefore the LED 28 is provided so as to be visibly confirmed. The other means of visibly confirming the operation or of notifying the user of the operation may be to notify by sounds or voices.

In case data are judged to be such, the code corresponding to the data will be output to a character generating circuit 64g, the corresponding character will be output to the color monitor 5 and the like through an adder 64f and the identification number and the like will be displayed in a character displaying area 5b adjacent to an endoscope picture image displaying area 5b.

The video signal inputting ends of the video disk device 8, still video device 9, printer 11, VTR 12 and monitor photographing device 13 are connected to the video signal outputting end 4b of the CCU 4 so that a video signal or photograph may be taken by a releasing 1operation.

Freezing and releasing switches 68a and 68b respectively instructing freezing and releasing are provided in the operating part 52 and are connected with the controller 65 through a signal line so that, for example, when the freezing switch 68 is ON, the controller 65 will prohibit writing a new picture image into the memory 64c and will output a still picture to the color monitor 5.

When the releasing switch 68b is operated, the controller 65 will control the still picture to be output and then will further output a releasing signal, for example, to the photographing device 13 which will photograph the still picture.

The peripheral devices or apparatus connected to the CCU 4 can be controlled also by a key input or the like from the keyboard 6 connected to the CCU 4. This keyboard 6 is characterized by being of a structure in consideration of the operability, water-proofness and wipability.

As shown in FIG. 3, the keyboard 6 comprises a keyboard body 21, a cable 22 extended out of this keyboard body and a connector not illustrated provided at the distal end of this cable 22 and removably connectable to the CCU 4.

Figure 4:
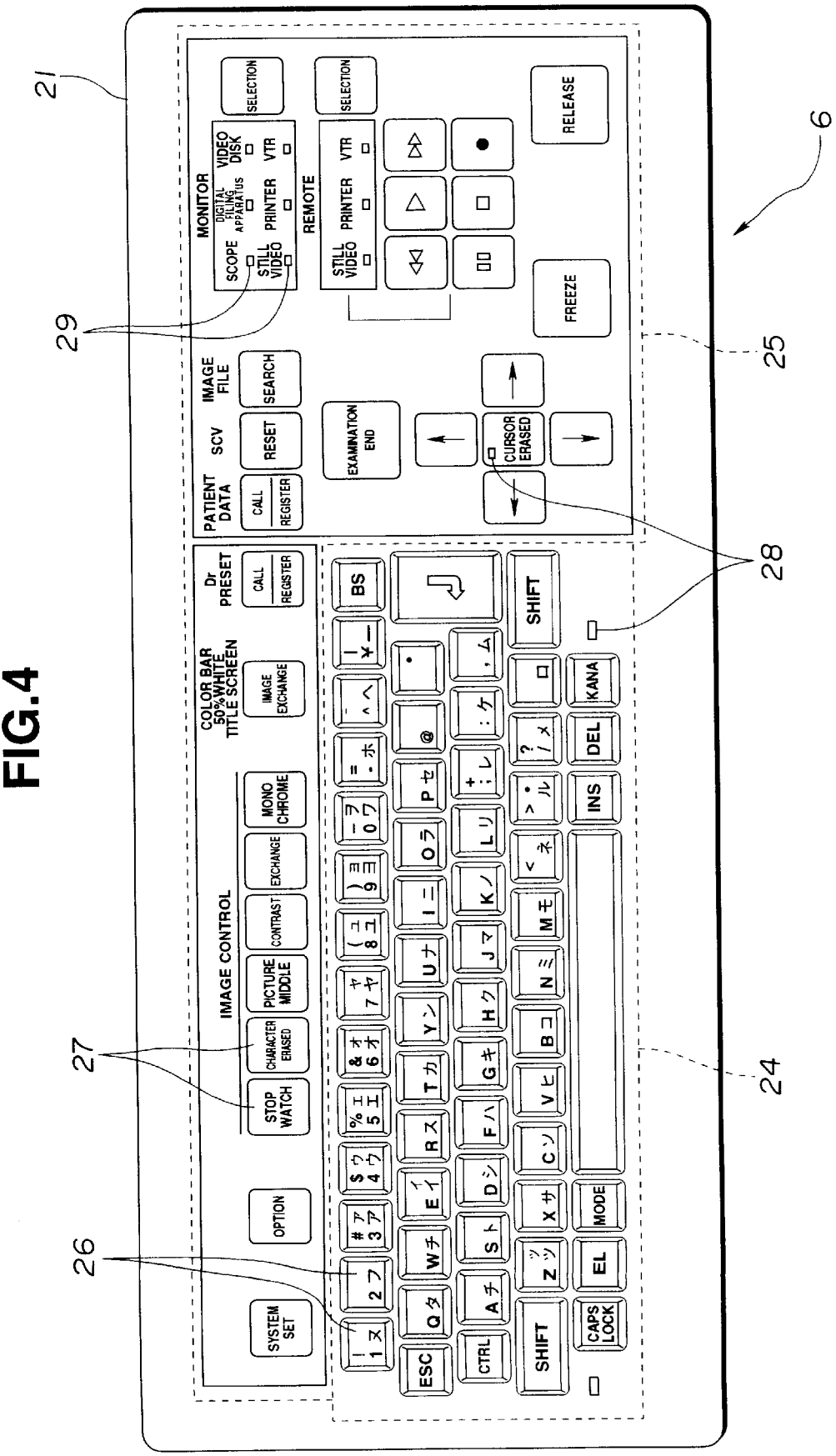

As shown in FIG. 3 or 4, the keyboard body 21 is provided on the upper surface with a data inputting part 24 for inputting data such as characters consisting of letters and signs and a function execution inputting part 25 inputting a function execution. This embodiment is highly characterized in that mechanical switches (abbreviated as mechaswitches hereinafter) 26 are adopted and formed as inputting keys (or switches) forming the data inputting part 24 and flat switches 27 are adopted and formed as inputting keys (or switches) forming the function execution inputting part 25.

The inputting keys forming the data inputting part 24 are so high in the using frequency by the operator in the general using environment that the mechaswitches 26 are formed by considering the operability to be important.

On the other hand, the inputting keys forming the function execution inputting part 25 are so lower in the using frequency by the operator than the data inputting part 24 in the general using environment that the flat switches 27 are formed by considering the water-proofness and wipability to be important.

For the above mentioned reasons, the inputting key forming the data inputting part 24 and the inputting key forming the function execution inputting part 25 as formed respectively of only the mechaswitches 26 and of only the flat switches 27 have been adopted and further the following reasons are considered.

That is to say, the data inputting part 24 is used to input such data as views or comments in most cases. In such case, only one or only several of the keys of the data inputting part 24 are little used. In general, the keys are used to input a considerable amount of data and are often used to input data related before and after.

Therefore, in order that the data may be smoothly input in such case, the inputting keys forming the data inputting part 24 are formed of only the mechaswitches 26. On the other hand, the inputting keys forming the function execution inputting part 25 are to execute the set function and therefore, in case they are actually used, only one or a few keys will be almost respectively used. Therefore, the function execution inputting part 24 is formed of the flat switches easy to clean.

Also, this embodiment is provided with an LED 28 which will light to show that the corresponding function is being executed when the keys forming the function execution inputting part 25 are pushed and will go out when the keys are pushed once again and an LED 29 showing which peripheral device is selected now.

Figure 5A:
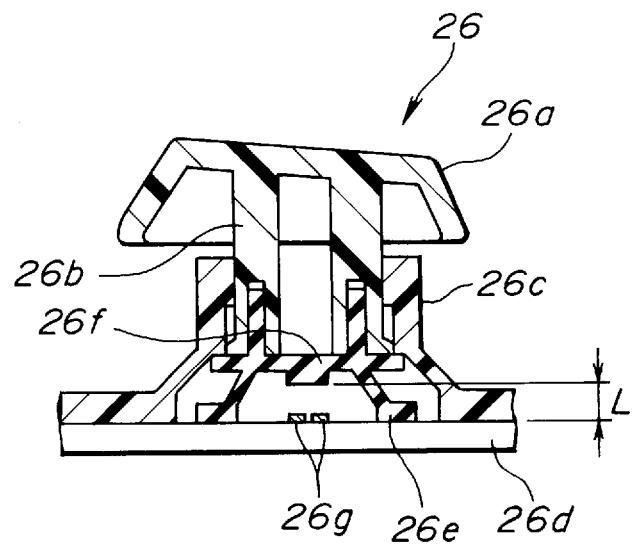
FIG. 5A is a sectioned view showing the structure of a mechanical switch.

An example of the structure of the mechaswitches 26 forming the above mentioned data inputting part 24 is shown in FIG. 5A.

A cylindrical sliding member 26b is provided on the underside of a key top 26a, is contained in an opening of a substantially cylindrical switch body 26c tapered to be wider on the lower end side and is slidable. A conductive rubber 26e having an elasticity and conductivity and secured at the lower end to a printed substrate 26d is contained inside the switch body 26c secured at the lower end to the printed substrate 26d.

This conductive rubber 26e has a thickened thick part 26f formed in the middle of the upper surface and is made conical on the side. A cylindrical part projects upward on the upper surface of this conductive rubber 26e and fits in a groove in the sliding member 26b of the key top 26a. When the key top 26a is pressed on the upper surface in this state, the sliding member 26b at the lower end will press the conductive rubber 26e on the upper surface and will transform and move the conductive rubber 26 to the printed substrate 26d side.

Two contact parts 26g are formed as a little separated from each other and opposed to the thick part 26f on the printed substrate 26d. Therefore, when the key top 26a is pressed on the upper surface to move the conductive rubber 26e to contact the printed substrate 26d, that is, to move the conductive rubber downward by about the stroke shown by the length L in FIG. 5A, the two contact parts 26g will be conducted by the thick part 26f of the conductive rubber 26, In case the key top 26a is pushed down, the downward movement of the key top 26a against the energizing force by the conductive rubber 26e will be able to be felt by the operating finger touch. In case the contact 26g on the lower side is contacted, the touch will be able to be felt. Therefore, even if the operation of the mechaswitch 26 is not confirmed with an eye, whether the mechaswitch 26 has operated to be ON or not will be able to be judged. That is to say, the mechaswitch 26 can be operated by a blind touch.

When a projection is provided on the pressing surface on the upper surface of the mechaswitch 26 in the reference position of many arranged mechaswitches 26, each finger is placed on the reference mechaswitch 26 having the projection and the objective mechaswitch 26 is moved from the reference position and is operated only when it is to be operated, even if the moving position of the finger is not confirmed with an eye, the objective mechaswitch 26 will be able to be operated.

On the other hand, the flat switch 27 is to be switched ON on the basis of the variation of the electric resistance by the pressing force of a thin sheet-shaped member. It is generally difficult to judge by the touch the variation by the pressing operation of this flat switch 27.

Figure 5B:
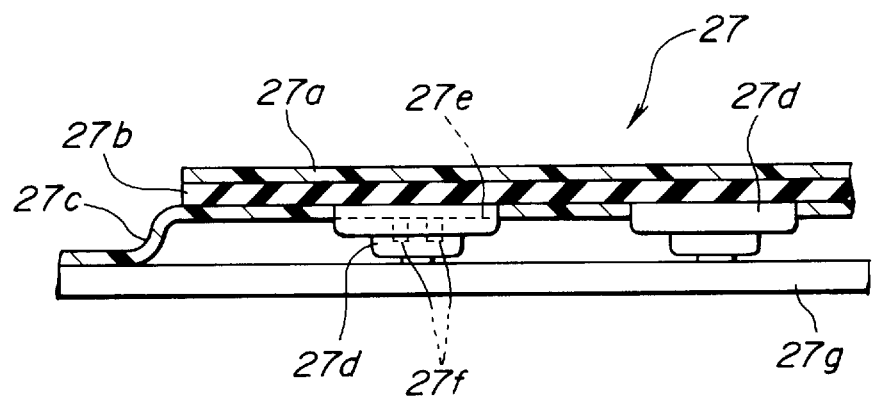

An example of the concrete formation of this flat switch 27 is shown in FIG. 5B.

A rubber damper 27b is provided below a water-proof surface sheet (or cover) and is supported by a panel 27c slightly projecting out of the periphery. Switches 27d are fitted to respective openings formed in the panel 27c and are substantially in contact with the conductive rubber 27e on the upper surface. Two contacts 27f are contained in each switch 27d and are electrically connected with the printed substrate 27g on the back surface side.

In the switch 27d covered with the water-proof sheet 27a and rubber damper 27b, when the conductive rubber 27e as an operating member on the upper surface is pressed downward from above through the sheet 27a and rubber damper 27b to be slightly downward moved or transformed, the electric resistance will be varied (for example, made smaller) by the compression and the internal contacts 27f will be substantially switched ON (the variation of this electric resistance is judged by the comparison with the threshold value by a comparator or the like as to whether they will be ON or not).

A structure which is other than the structure shown in FIG. 5B, eliminates the physical contact by confirming that the key is ON/OFF by a sensor as in a touch screen and is made flat is also considered to be a part of the flat switch.

Therefore, in the case of such flat switch 27, even if a finger is mounted on the flat switch 27, the ON/OFF operating stroke will be so small that it will be hard with the finger operating touch to judge whether the switch is ON or not by the pressing operation and therefore it will be difficult to operate with a blind touch.

On the other hand, as the flat switch 27 has substantially no movable part, each flat switch 27 can be easily made of a water-proof structure with such cover member as the water-proof sheet 27a and can be made of a water-proof structure by covering the flat switch 27 and the part around it where the flat switch 27 is not provided with the sheet-shaped cover members.

The cover member to be used for a water-proof structure can be made also proof against a disinfection with a disinfecting liquid or a sterilizing treatment by using a chemicals-proof material proof against such disinfecting liquid and sterilizing chemical liquid as alcohol. A highly wipable structure on which dusts can be easily wiped off by a simple wiping operation is made by using a cover member processed on the surface so as to be easy to wipe off dusts or by using a cover member with a material on which dusts are hard to be deposited.

By the way, the structures of the mechaswitch and flat switch may be formed of membranes or metal contacts (switches in which metal pieces are used for contacts).

In the case of the system formation shown in FIG. 1, the features of the concrete functions realized by the keyboard 6 of this embodiment shall be concretely explained in the following on the case of the keys shown in FIG. 3 or 4.

In the data inputting part 24, keys in which the operator inputs such characters and signs as alphabets and Kana letters are arranged and a character and sign are printed on the mechaswitch 26 forming each key.

As the part is formed of the mechaswitch 26 as described above, a stroke is in the operation of the key and is high in the operability.

Therefore, the operator can input characters and signs by a blind touch.

On the other hand, the function execution inputting part 25 is formed of the flat switches 27 as described above and is used for the operator to execute functions. This part is covered with a water-proof cover and is high in the wipability, water-proofness and chemicals-proofness.

Therefore, it can have the deposit easily wiped off and can be disinfected by being wiped, for example, with alcohol.

As shown in FIG. 3 or 4, the function execution inputting part 25 is arranged on the periphery of the data inputting part 24. The data inputting part 24 is collectively arranged on the operator side (on the lower side in FIGS. 3 and 4) operable for the operator so that characters may be easy to input by a blind touch. The function execution inputting part 25 which is lower in the using frequency than the data inputting part 24 is formed on its periphery (on the upper side and right side in FIGS. 3 and 4). The function execution inputting part 25 is divided into groups in a manner such that the flat switches 27 each having the same function belong to the same group.

The LED 28 will light to show that a function is being executed when the key is pushed and will go out when the key is pushed once again. The LED 29 shows which peripheral device is now selected.

The keys forming the function execution inputting part 25 have respective predetermined functions allotted to so that, when the respective keys are operated, respective functions allotted as in the following will be executed.

The system setting keys set various parameters of the system.

The option key will cope with softwares (for example, by displaying a function menu) without adding keys in case there is an additional function.

The stop watch key is to measure time. The time is displayed in the displaying device (such as the color monitor or LCD).

The character erasing key is to erase displayed characters of the displaying device.

The picture middle key is to move the picture image to the middle of the displaying device.

The contrast key is to vary the contrast of the picture image.

The exchanging key is to exchange the positions of the moving picture and still picture.

The monochromatic key is to change the picture image from the color to be monochromatic.

The picture switching key is to switch the following functions whenever it is pushed:

(a) The color bar is displayed in the color monitor 5 as a displaying device;
  (b) White (50% white) intermediate between white and black is displayed in the displaying device; and
  (c) The video (ordinary observed picture) in the displaying device is switched to the title picture (picture displaying characters in the entire picture).

The Dr preset registering/calling key is for the user to be able to memorize or call out environment setting parameters of the apparatus.

The patient data registering/calling is for the user to be able to memorize or call out the patient data.

The SCV resetting key is to reset the counter of the SCV (monitor photographing device 13).

The picture image file searching key is to search the picture image file of the picture image filing apparatus.

The inspection end key is to erase the data input before and make an environment of inputting new data.

The cursor erasing key is to erase the cursor displayed in the displaying device.

The monitor selecting key is to select the peripheral device in which the video signal is to be input.

The remote selecting key is to select the peripheral device which remote-operates from the keyboard 6 such functions as the picture recording, reproducing, winding back, quick feeding and posing.

The freezing key is to still the moving picture to be a still picture.

The releasing key is to connect the peripheral device which can record the picture image to record the picture image.

→, ←, ↑, ↓ are to move the cursor and character inputting place.

In this first embodiment, the function execution inputting part 25 which the operator can operate mostly with the dirty hand is formed of the flat switch 27, the data inputting part 24 to input data mostly with the hand not dirty is formed of the mechanical switch 26, the function execution inputting part 25 can be simply made clean and the mechanical switch 26 forming the data inputting part 24 is adapted to input data in a high operability. Concretely, in case the endoscope inspection, diagnosis or therapy is made by the electronic endoscope system 1 using the scope 2, if the above mentioned keyboard 6 is used, the operation will be able to be made in a state adapted to the using environment as in the following:

For example, in case the endoscope inspection is to be made on a patient, before the scope 2 is used, such data as the name of the patient will be input. In such case, by the data inputting part 24 formed of the mechaswitch 26, the data will be able to be simply input in a high inputting operability.

Then, in case an affected part or the like is to be inspected or treated by using the scope 2, such operation as making the endoscope picture image displayed in the color monitor 5 a still picture from the moving picture or recording it with the peripheral device will be often made and will be made substantially by the operation of the key of the function executing part 25.

Therefore, even if the operator operates the apparatus with a dirty hand, if he wipes it with alcohol or the like after the use, the dirt will be able to be simply removed and the apparatus will be able to be made clean.

In case such data as views are to be input after the endoscope inspection, they will be able to be input with a clean hand and therefore will be able to be input simply in a high inputting operability by the data inputting part 24 formed of the mechaswitch.

Figure 6:
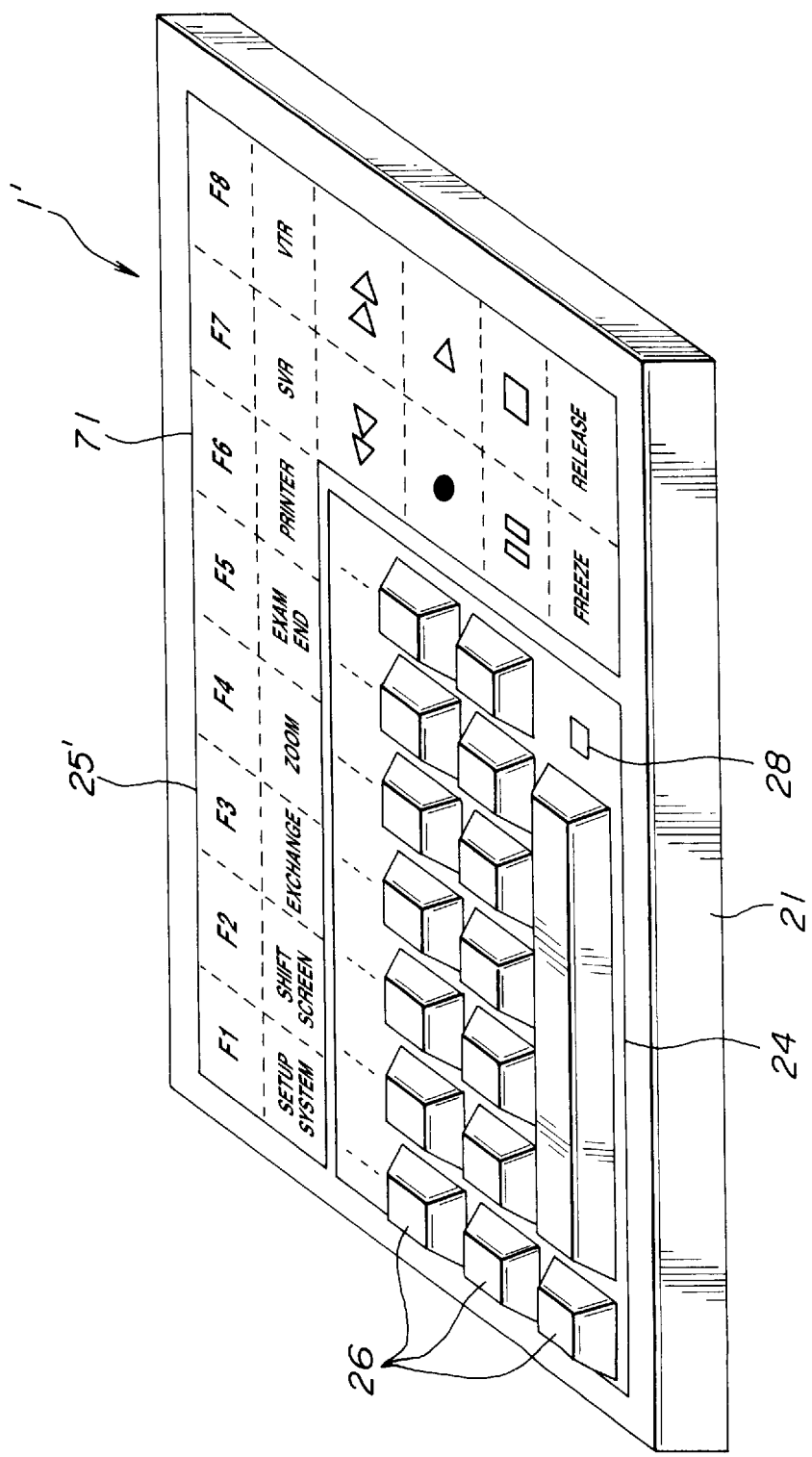
FIG. 6 is a perspective view showing the schematic formation of the medical keyboard apparatus of a modification of the first embodiment.

FIG. 6 shows a keyboard 6' of a modification of the first embodiment of the present invention. Whereas, in the keyboard 6 of the first embodiment, the function execution inputting part 25 is formed of the flat switch 27, in this modification, the function execution inputting part 25 ' is formed of a touch screen 71.

This touch screen 71 is provided with a transparent touch sensor as a function instructing key on the instructing part, for example, by an LCD. Each touch sensor is formed, for example, of a pair of transparent electrodes and a transparent conductive rubber switching ON/OFF the pair of electrodes. The controller 65 in FIG. 2 to which this keyboard 6' is connected judges that the part of the pair of electrodes will be operated in case the resistance of each pair of electrodes is below a fixed value.

The controller 65 displays its function to the LCD forming the touch screen 71 through an LCD driving circuit.

The operation of this modification is substantially the same as of the first embodiment. This modification has a merit that the executed function and change can be simply made by the change of the program. That is to say, the executed function can be changed in softwares by the program and the display of the executed function can be also changed in softwares. The other effects are substantially the same as of the first embodiment.

Figure 7:
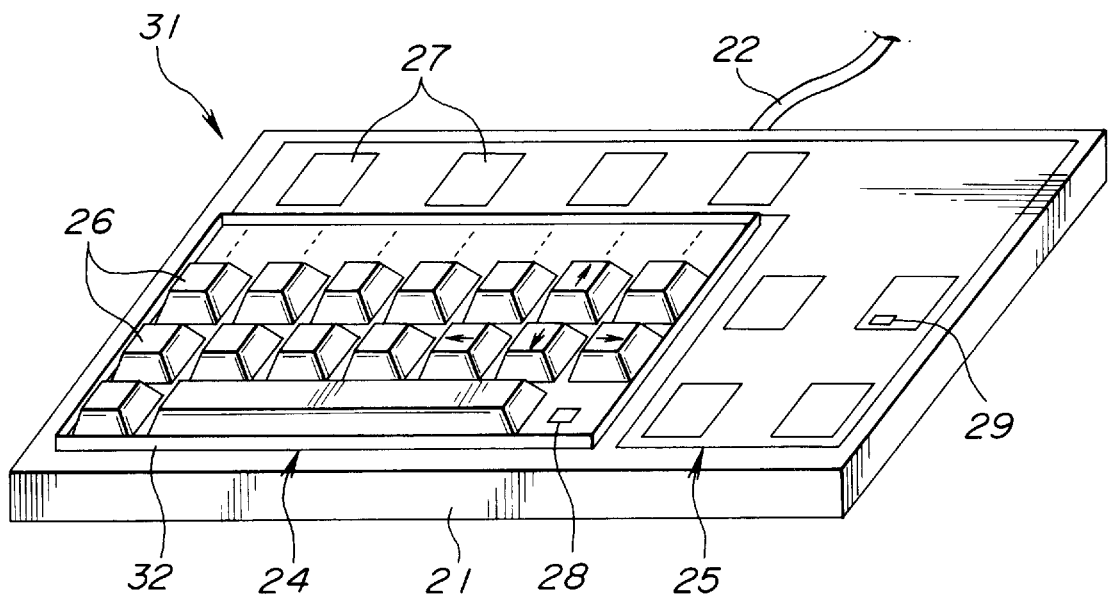
FIGS. 7 and 8 relate to the second embodiment of the present invention.
Figure 8:
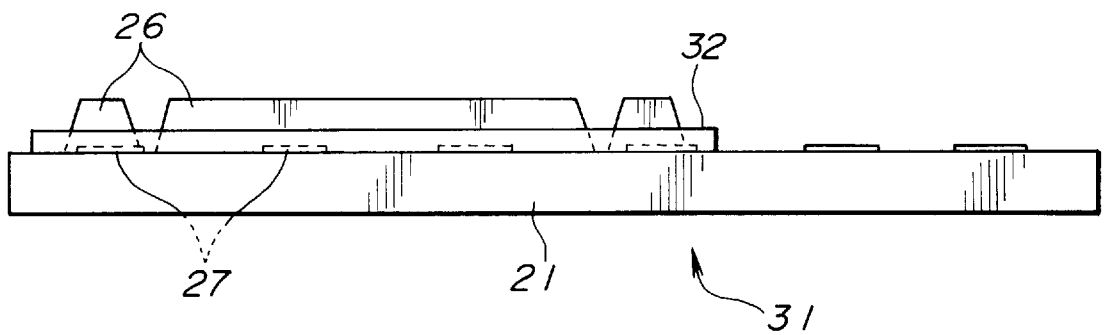

The second embodiment of the present invention shall be explained in the following. FIG. 7 shows in perspective the schematic formation of the keyboard of the second embodiment of the present invention. FIG. 8 is an elevation showing the schematic formation.

The keyboard 31 of this second embodiment is provided with such partition member 32 as is illustrated between the function execution inputting part 25 and data inputting part 24 in the keyboard 6 of the first embodiment.

This partition member 32 is to cover the periphery of the data inputting part 24 with a chemicals-proof plate.

This partition member 32 will prevent dusts or liquids from being deposited on the mechaswitch 26 when the function execution inputting part 25 is wiped, for example, with cloth or the like.

The cursor moving key is provided on the function execution inputting part 25 side in the first embodiment but is provided on the data inputting part 24 side in this second embodiment.

The other formations are the same as in the first embodiment. The same components shall bear the same signs and shall not be explained here.

This second embodiment has the same operation or function as of the first embodiment and can be further protected by the partition member 32 so that, even in case the function execution inputting part 25 is worked to be cleaned, dust or liquids will be prevented from being deposited on the mechaswitch 26.

Figure 9:
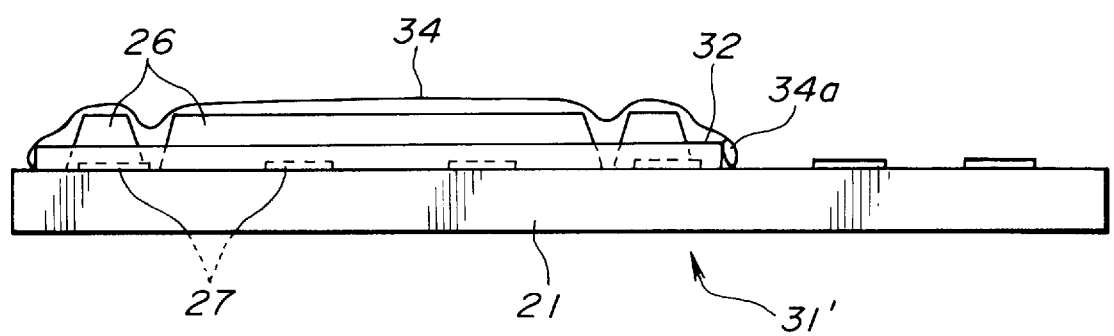
FIG. 9 is an elevation showing the schematic formation of a medical keyboard apparatus of the third embodiment of the present invention.

The third embodiment of the present invention shall be explained in the following. FIG. 9 is an elevation of the keyboard of the third embodiment of the present invention and shows the schematic formation.

The keyboard 31' of this third embodiment is further provided with a thin cover 34 covering the data inputting part 24 in the keyboard 6 of the first embodiment or the keyboard 31 of the second embodiment. This cover 34 covers the data inputting part 24 on the upper side, is provided at the end with such elastic fixing part 34a as a rubber band and is elastically fitted to the partition member 32 on the outside surface, for example, in the second embodiment.

Figure 10:
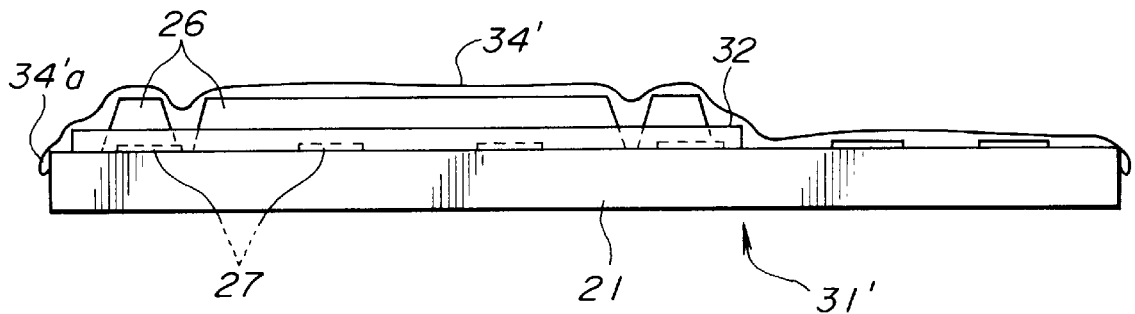
FIG. 10 is an elevation showing the schematic formation of a medical keyboard apparatus of a modification of the third embodiment.

However, if necessary, the keyboard body 21 including not only the data inputting part but also the function execution inputting part may be covered at least on the upper surface side with the thin cover 34' as in the modification in FIG. 10. In FIG. 10, the rubber band 34'a at the end of the cover 34' is elastically fixed to the side of the keyboard body 21.

Otherwise than the structure shown in FIG. 10, the entire keyboard body 21 may be covered to be enclosed. (Further, as required, the cable 22 may be covered with the cover 34' or another cover.) This cover 34 or 34' is formed to be thin of a transparent and extensible member. Each mechaswitch 26 wherein the data inputting part 24 is covered as in FIG. 8 and is formed thereon can be operated. The degree of the extensibility of the cover 34, the stroke amount of the mechaswitch 26 to be ON and the height are so set that the adjacent mechaswitch may not be ON in case the mechaswitch 26 is operated. The cover 34 or 34' is waterproof so that, even if each mechaswitch 26 forming the data inputting part 24 is operated from above the cover with a dirty hand or a hand on which blood is deposited, each mechaswitch will not be stained.

The others are of the same formation as of the first or second embodiment. The operation and effect of this third embodiment or its modification can protect the function execution inputting part 25 from being stained in addition to those of the second embodiment. Further, according to this third embodiment or its modification, even in case it is necessary to input a comment or the like with a hand (or glove) having touched the patient, for example, as during the diagnosis, the main switch of the data inputting part 24 will be able to be prevented from being stained.

For example, the cover 34 may be used as a disposable cover which is abandoned after the endoscope inspection so that a new clean cover 34 may be fitted and used before the next endoscope inspection. The used cover 34 disinfected with a disinfecting liquid or the like after the endoscope inspection may be reused. The cover 34' may be also made the same.

Figure 11:
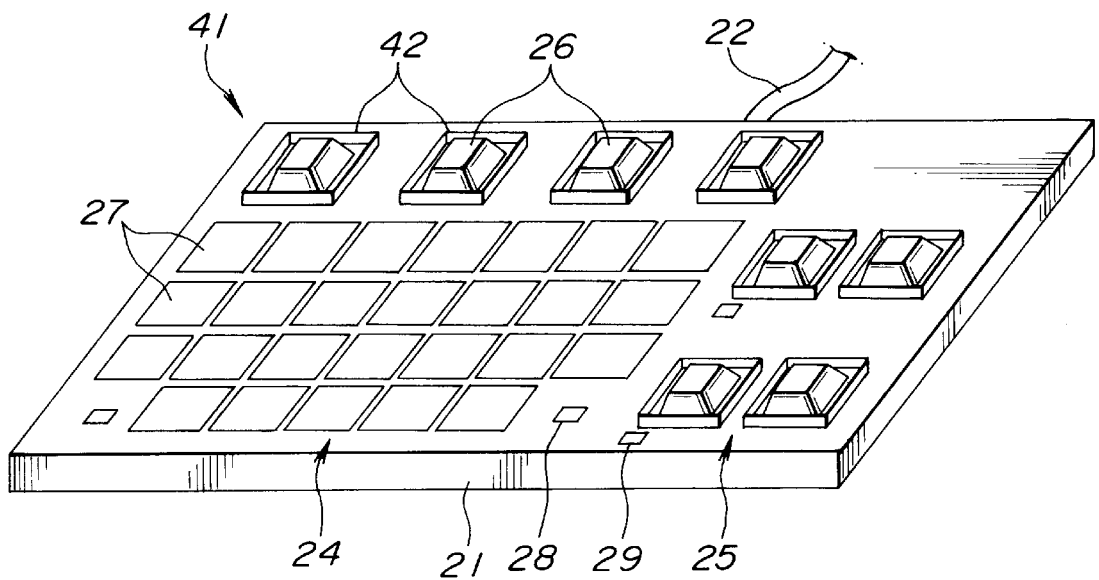
FIGS. 11 and 12 relate to the fourth embodiment of the present invention.
Figure 12:
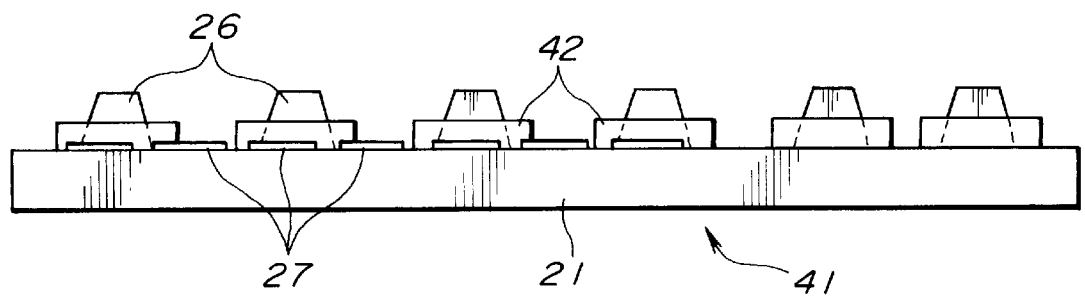

The fourth embodiment of the present invention shall be explained in the following. FIG. 11 shows in perspective the schematic formation of the keyboard of the present invention. FIG. 12 shows in elevation the schematic formation.

The keyboard 41 of this fourth embodiment is of a formation having the data inputting part 24, function execution inputting part 25 and LED's 28 and 29 the same as in the first embodiment.

This fourth embodiment is characterized in that the data inputting part 24 is formed of the flat switches 27 and the function execution inputting part 25 is formed of the mechaswitches 26.

Also, each mechaswitch 26 is enclosed on the periphery with the partition member 42 so that dusts or liquids may not enter each mechaswitch 26.

In this embodiment, the using frequency by the operator is so high that the part well touched and therefore the part likely to be dirty are made easy to sweep.

The function execution inputting part 25 is formed of the mechaswitches so as to be easy to operate.

The partition member 42 is provided on the periphery of each mechaswitch 26 so that dusts or liquids may not enter the mechaswitch 26.

In this embodiment, the using frequency by the operator is higher than in the prior reference formed of only the mechaswitches and the data inputting part 24 which is a well touched part is formed of the flat switch 24 so as to be easy to wipe and sweep to be clean.

Particularly, the keys of the data inputting part 24 are so arranged that many keys may concentrate. Therefore, when dusts enter the space between the keys, the removing work will be difficult. Therefore, the data inputting part 24 is formed of the flat switches 27 so that the dust removing work may be made simple. Thereby, though the operability reduces, the trouble of the work can be reduced and user considering the reduction of the working trouble to be important can be coped with.

According to this fourth embodiment, as a part is formed of the mechaswitches 26, the operability will improve. Also, dusts are hard to enter the space between the keys, no trouble will be likely to occur. As it has the flat switches, the wipability and water-proofness of that part will improve.

As there is the partition between the flat switches 27 and mechaswitches 26, even if the flat switches 27 are wiped, dusts and liquids will be hard to come to the mechaswitches 26.

By the way, in this fourth embodiment, each mechaswitch 26 forming the function execution inputting part 25 may be covered with a cover so as to be operable as covered. Such formation is adapted to the keyboard used particularly in the midst of the endoscopic inspection.

That is to say, even in the case of operating with a hand having touched the patient during the operation, the operability will be high and, even if it is necessary to input a comment or the like, as the flat switches 27 are used, even if they are stained, they will be able to be simply cleaned.

Figure 13:
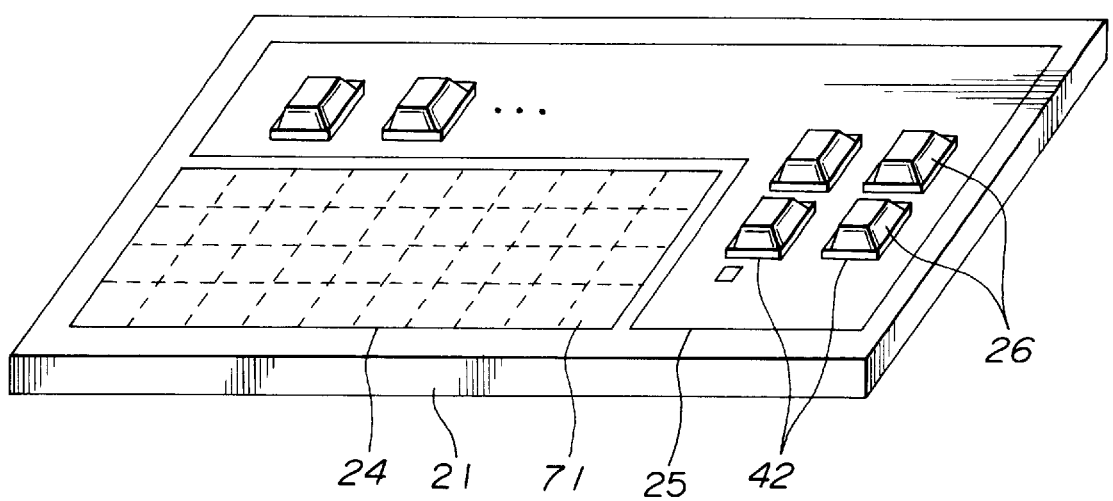
FIG. 13 is an elevation showing the schematic formation of a medical keyboard apparatus of a modification of the fourth embodiment.

FIG. 13 shows the keyboard 41' of the modification of the fourth embodiment. In this modification, the data inputting part 24 in the fourth embodiment is formed of a touch screen 71 instead of the flat switches 27.

This modification has the same merit as in the case explained in FIG. 6.

By the way, in the above described embodiment, an apparatus formed of mechanical switches different, for example, in the stroke amount may be prepared so that the apparatus which the user can select and use may be further expanded. The partitioning with the partition member is not limited to enclosing with a plate shape and a shape in which, for example, the cross-section is semicircular and the central part is convex may be used.

Further, the above mentioned apparatus is removably fitted to the CCU. Therefore, in case the system to be used is the same, the keyboard may be replaced and used in response to the cases that the function execution inputting part 25 is mostly used and that the data inputting part 24 is mostly used. Also, a plurality of different keyboards may be connected so that the keyboard easy to use may be selected and used in response to the using environment.

By the way, in the first embodiment, the flat switch 27 as adapted to the function execution inputting part 25 is shown in FIG. 5B. However, the structure in FIG. 5B which is large in the ON/OFF operation stroke may be adopted (the water-proof sheet 27a and rubber damper 27b are also made of extensible materials in response to this). That is to say, the function execution inputting part may be formed of flat and water-proof cover fitted switches.

Also, different embodiments formed by partly combining the above described embodiments belong to the present invention.

What is claimed is:

1. An endoscope system comprising:

an endoscope having an elongate inserted part, an illuminating light projecting means projecting an illuminating light out of the distal end of said inserted part, an objective optical system formed on a distal end of said inserted part and forming an image of an object illuminated by said illuminating light, and an imaging device photoelectrically converting the image based on said objective optical system;

a signal processing unit for effecting a signal processing to said imaging device of said endoscope to produce an endoscope picture image;

a peripheral apparatus including a digital filing apparatus capable of storing and editing said endoscope picture image;

a controlling device connected to said signal processing unit and said peripheral apparatus for controlling said signal processing unit and said peripheral apparatus;

a keyboard, connected to said controlling device, having a data inputting part for inputting data including characters and a function execution inputting part to input instructions to execute a plurality of preset functions of said signal processing unit and said peripheral apparatus;

a displaying means for displaying said endoscope picture image produced by said signal processing unit and said characters;

a plurality of mechanical switches forming said data inputting part and each having a long stroke on which a contact is switched;

a plurality of flat switches forming said function execution inputting part, said flat switches each having substantially no stroke on which a contact is switched and being covered with a water-proof cover;

an informing means, associated with said keyboard, for indicating successful operation of one of said plurality of flat switches to the operator whenever one of said plurality of flat switches is acceptably operated; and a command judging means, included in said controlling device, for judging whether the input from the keyboard comprises instructions corresponding to the plurality of preset functions or character data;

wherein when said judging means judges that the input from the keyboard comprises an instruction corresponding to a preset function by operation of a flat switch of the function execution inputting part, the controlling device controls the informing means associated with the keyboard to indicate to the operator that the operation of the flat switch has been accepted and executes the corresponding preset control function.

2. An endoscope system according to claim 1, wherein said informing means consists of an LED.

3. An endoscope system according to claim 1, wherein said data inputting part is arranged on a side of said keyboard near to a user operating said keyboard.

4. An endoscope system according to claim 1, wherein said function execution inputting part is arranged on a periphery of said data inputting part.

5. An endoscope system according to claim 1, wherein a partition member is located on a periphery of said data inputting part for preventing dust and liquid from entering said data inputting part.

6. An endoscope system according to claim 1, wherein a partition member is located on a periphery of said plurality of mechanical switches for preventing dust and liquid from entering said plurality of mechanical switches.

7. An endoscope system according to claim 1, wherein said data inputting part is covered with a transparent thin cover such that said plurality of mechanical switches are operable from above said cover.

8. An endoscope system according to claim 7, wherein said cover is removably fitted to said keyboard.

9. An endoscope system according to claim 7, wherein said cover is water-proof.

10. An endoscope system according to claim 1, wherein said data inputting part and said function execution inputting part are covered with a transparent thin cover such that said plurality of mechanical switches and said plurality of flat switches are operable from above said cover.

11. An endoscope system according to claim 1, wherein said plurality of flat switches are formed by a touch screen to be switched on by the touch of a finger of a user.

12. An endoscope system according to claim 1, wherein said data inputting part inputs characters comprising letters, signs and graphic data.

13. An endoscope system according to claim 1, wherein said contacts of said plurality of mechanical switches are mechanically switched on, by the operation of moving by a predetermined stroke, the operating member forming each of said plurality of mechanical switches, and wherein said plurality of flat switches are covered with a water-proof cover as said waterproof function and said contacts of said plurality of flat switches are switched on by a slight movement or transformation of the operating member forming each of said plurality of flat switches.

14. An endoscope system according to claim 1, wherein said peripheral apparatus includes a video printer printing said endoscope picture images on papers.

* * * * *